United States Patent [19]

Fields

[11] 4,405,523

[45] Sep. 20, 1983

[54] PROCESS FOR PREPARATION OF BENZOPHENONE, ANTHRAQUINONE AND O-DIBENZOYLBENZENE

[75] Inventor: Ellis K. Fields, River Forest, Ill.

[73] Assignee: Standard Oil Company (Indiana), Chicago, Ill.

[21] Appl. No.: 361,398

[22] Filed: Mar. 24, 1982

[51] Int. Cl.$^3$ .................... C07C 50/18; C07C 69/76; C07C 49/657

[52] U.S. Cl. .................... 260/369; 560/109; 568/319

[58] Field of Search .................... 260/369; 560/109; 568/319

[56] References Cited

U.S. PATENT DOCUMENTS

| | | | |
|---|---|---|---|
| 2,528,789 | 11/1950 | Sachanen et al. | 568/323 |
| 2,859,247 | 11/1958 | Radzitsky | 564/36 |
| 3,002,024 | 9/1961 | Blomiquist | 260/369 |
| 3,277,184 | 10/1966 | Ryland et al. | 560/109 |
| 3,699,135 | 10/1972 | Armbrust et al. | 260/369 |
| 3,872,135 | 3/1975 | Reinicke et al. | 260/369 |
| 4,002,653 | 1/1977 | Reuter et al. | 260/369 |
| 4,036,860 | 7/1977 | Engelbach et al. | 260/369 |
| 4,036,861 | 7/1977 | Togo et al. | 260/369 |
| 4,215,063 | 7/1980 | Schmitt, Jr. et al. | 260/369 |
| 4,305,879 | 12/1981 | Sugio et al. | 260/369 |

OTHER PUBLICATIONS

*Journal of Organic Chemistry*, vol. 25, pp. 269–272, 1960, Jensen "Preparation of O-dibenzoylbenzene and o-dibenzoylbenzene.

*Primary Examiner*—Delbert E. Gantz
*Assistant Examiner*—Raymond Covington
*Attorney, Agent, or Firm*—William C. Clarke; William T. McClain; William H. Magidson

[57] ABSTRACT

Process for the concurrent synthesis of benzophenone, anthraquinone, and o-dibenzoylbenzene by pyrolysis of benzoic acid salts of yttrium, erbium, and dysprosium and mixtures thereof at temperatures of from about 200° C. to 500° C. and a pressure of about 0.1 to about 100 atmospheres. In an alternative method, a benzoic acid compound is passed through an oxide of yttrium, erbium, dysprosium and mixtures thereof in the presence of steam.

12 Claims, No Drawings

PROCESS FOR PREPARATION OF BENZOPHENONE, ANTHRAQUINONE AND O-DIBENZOYLBENZENE

BACKGROUND OF THE INVENTION

This invention relates to a process for the preparation of benzophenone, anthraquinone and o-dibenzoylbenzene, and their substituted derivatives.

In general, the common methods of synthesis of ketones can be divided into (1) synthesis from acid halides and organometallic compounds, (2) synthesis from carboxylic acids, (3) Friedel-Crafts reactions, and (4) enolate condensations.

Synthesis from acid halides and organometallic compounds has been extensively used but costs of the organometallic reagents are relatively expensive and care must be used in handling. The use of carboxylic acids and their salts for ketone synthesis suffers from the disadvantage that the method will produce in general only the symmetrical ketones in good yields. The Friedel-Crafts acylation reactions generally give good yields. However, their use is restricted by the orientation of the acyl group introduced and the metal halides are expensive with attendant waste disposal problems. Enolate condensations give a variety of products; however, the overall yields are frequently not so good as those that can be obtained by other methods, and procedures frequently are more involved.

As is well-known, the important methods of formation of benzophenone, i.e., benzophenone, and its substituted derivatives are the following: (1) oxidation of diphenylmethanes or benzhydrols, e.g., by chromic acid or by oxygen in presence of a catalyst, for example, as is taught in U.S. Pat. No. 2,859,274; (2) hydrolysis of ketone chlorides; (3) condensation of benzoyl halides with benzene, its homologues, and substituted derivatives having a reactive position, in presence of $AlCl_3$ or other catalyst, or under high pressure, as taught in U.S. Pat. No. 2,528,789; (4) reaction of a benzonitrile (or benzoyl halide) with a phenylmagnesium halide; (5) distillation of calcium or other suitable benzoate (Ann. 12, 41).

Preparation of anthraquinone specifically has been proposed by several different processes: (1) the Diels-Alder reaction of butadiene on 1,4-naphthoquinone, (2) oxidation of anthracene in the presence of catalysts, (3) Friedel-Crafts reaction with benzene and phthalic anhydride, (4) oxidation of suitable precursors such as indane. In the Friedel-Crafts process, since a large amount of aluminum chloride is necessary, disposal of the wastes from the process is difficult. Furthermore, since isomerization reactions, rearrangement reactions, and elimination reactions occur in the process, many by-products derived from these reactions contaminate the product. Oxidation of anthracene is economically accomplished only when relatively pure anthracene is available at moderate costs. The Diels-Alder reaction suffers from the high cost of naphthoquinone. U.S. Pat. Nos. 2,794,813; 3,699,134; 3,872,134; 3,872,135; 4,002,653; 4,036,860; 4,036,861; and 4,215,063 teach typical processes for manufacture of anthraquinone by oxidation of diphenylmethane compounds. These processes produce many by-products.

o-Dibenzoylbenzene has been reported as most satisfactorily prepared by a reaction carried out by adding phenylmagnesium bromide to a solution of phthaloyl chloride in ether at $-55°$ C. (F. R. Jensen, *J. Org. Chem.*, 25, 269 (1960)). The product forms an ether-insoluble complex with magnesium bromide. Addition of water liberates the o-dibenzoylbenzene. However, the yield of o-dibenzoylbenzene prepared by this complicated method is reported as poor (32%).

As a result of these difficulties, considerable investigations have been carried out in efforts to develop synthesis of benzophenone, anthraquinone and o-dibenzoylbenzene whereby the desired products in good yield are obtained by simple economic methods, without problems of waste disposal. This invention relates to a method for pyrolysis of yttrium, erbium, or dysprosium salts of benzoic acid whereby benzophenone, anthraquinone, and o-dibenzoylbenzene are produced in good yield. The process can be by batch or by continuous method.

SUMMARY OF THE INVENTION

Process for concurrent preparation of benzophenone, anthraquinone and o-dibenzoylbenzene and their substituted derivatives by pyrolysis of benzoic acid salts of yttrium, erbium, dysprosium or mixtures thereof in an inert atmosphere at a temperature of from about 350° C. to about 600° C. at a pressure of from 0.1 to 100 atmospheres. In an alternative method, a benzoic acid compound is passed through an oxide of yttrium, erbium, dysprosium or mixtures thereof in the presence of steam.

DETAILS OF THE INVENTION

The process of the instant invention relates to a synthesis of benzophenone, anthraquinone, and o-dibenzoylbenzene from benzoic acid salts or oxides of yttrium, erbium, dysprosium or mixtures thereof. In one method the acid salts are pyrolyzed in an inert atmosphere at a temperature within the range of from about 350° C. to about 600° C. and at a pressure of from 0.1 to about 100 atmospheres. Yields of by-products are minimized. Use of benzoic acid salts of the metals specified requires pyrolysis conditions for periods of from 2 to 10 minutes. The products of pyrolysis are taken up in suitable solvents such as acetone, benzene, toluene, isopropanol, or cyclohexane. Product is recovered by evaporation of the solvent. Separation of product is by conventional methods such as crystallization and distillation. In an alternative method, the process can be performed in a continuous manner by the passage of benzoic acid in the presence of steam at a temperature within the range of from about 200° C. to about 500° C. and 0.1 to 100 atmospheres through the metal oxides of yttrium, erbium, dysprosium and mixtures thereof.

The oxides of yttrium, erbium, dysprosium, or mixtures thereof, recovered as products of the pyrolysis, are reused in a simple, economic method by reaction with benzoic acid to yield the process starting materials in the absence of steam.

Substituted salts of benzoic acid can be used to prepare substituted compounds of benzophenone, anthraquinone, and o-dibenzoylbenzene in the instant invented process. Suitable substituents are the halogens (chlorine, bromine, iodine, and fluorine), methyl groups, nitro groups, alkoxy groups, aryloxy groups, amino groups, and dialkylamino groups. Suitable compounds are p-chlorobenzoic and p-toluic acid, m-methoxybenzoic acid, p-dimethylaminobenzoic acid.

An inert atmosphere is an essential element of one method of the process of the instant invention using benzoic acid salts to prevent undesired by-products.

Suitable inert atmospheres can be of nitrogen, carbon dioxide, helium, argon, and mixtures thereof. Nitrogen is preferred because of availability and purity when obtained commercially.

Pressures of from 0.1 to 100 atmospheres can be used. Under circumstances of less stable constituents, a vacuum, that is about 0.1 atmosphere pressure, can be desirable. Under ordinary circumstances, increases pressures greater than atmospheric, up to 100 atmospheres pressure will be advantageous.

It has been found that benzoic acid salts of yttrium, erbium, dysprosium and mixtures thereof can be pyrolyzed to yield the useful products, benzophenone, anthraquinone, and o-dibenzoylbenzene. Benzoic acid salts other than those of yttrium, erbium, dysprosium and mixtures thereof are not suitable. For example, sodium benzoate and potassium benzoate, when pyrolyzed under the conditions required by the invented process, yielded minimal amounts of benzophenone, no anthraquinone or o-dibenzoylbenzene, and small quantities of many phenyl compounds. Most of the product in each case was an insoluble char.

Benzophenone, anthraquinone, and o-dibenzoylbenzene are separated easily by distillation as their boiling points are widely different. Benzophenone is useful in perfumes, pharmaceuticals, and insecticides (Kirk-Othmer, *Encyc. of Chem. Tech.* 2, 478 (1948); in light-sensitive compositions, Ger. No. 2,357,642; as a sensitizer for degradation of discarded polyolefins, Ger. No. 2,263,879; as a catalyst for cross-linking polyesters, U.S. Pat. No. 3,959,103, as well as in many other uses.

Anthraquinone is well-known as the base material for the manufacture of a group of dyes having, unsurpassed fastness properties as a class (Kirk-Othmer, *Encyc. of Chem. Tech.* 2, (1948).

o-Dibenzoylbenzene is useful in the preparation of polymers with diamines (A. A. Volpe, et al., *J. Macromal. Sci. Chem.*, 1969, 1087) and as a photochemical sensitizer (*J.A.C.S.*, 86, 4536 (1964)).

The benzoic acid salts useful in the instant invention are prepared readily by precipitation from an aqueous solution of the chlorides or nitrates with 3 mole equivalents of aqueous sodium benzoate. Alternatively, the metal oxides of yttrium, erbium, dysprosium or mixtures thereof can be heated with benzoic acid at a temperature within the range of from about 200° C. to 500° C. to give the benzoates. Another method of practicing the instant invention, in a continuous process is considered to comprise the passage of benzoic acid in the presence of steam through the metal oxides of yttrium, erbium, dysprosium or mixtures thereof at a temperature within the range of from about 200° C. to 500° C. and from about 0.1 to about 100 atmospheres to give the products of benzophenone, anthraquinone, and o-dibenzoylbenzene directly. The product is extracted with an aqueous sodium bicarbonate solution to remove unreacted benzoic acid, and then is filtered and dried. The product, which is insoluble in aqueous bicarbonate or similar mild base, is analyzed by gas chromatography. Steam is essential to activate the oxides of yttrium, erbium, and dysprosium or mixtures thereof as these oxides are typically unreactive at temperatures within the range of 200° C. to about 500° C.

The invention will be illustrated by reference to the following specific examples.

EXAMPLE I

Dry yttrium benzoate, 9.04 g, 20 mmoles, was heated in a Vycor tube with a takeoff and cooled receiver under nitrogen at 100 cc/min. At 350° C. decomposition started, as evidenced by the evolution of gas. After 30 minutes the temperature was increased to 500° C. and kept there for 10 minutes longer. The pyrolysate was taken up in acetone, the cooled contents of the Vycor tube were extracted with acetone, the combined acetone extracts were filtered and evaporated to give 3.7 g of yellow solid. Analysis by gas chromatography of the solid was: 39.7 wt% benzophenone, 4.8 wt.% anthraquinone, and 16.8 wt% o-dibenzoylbenzene. There was no detectable m- or p-dibenzoylbenzene.

The tube contents remaining after extraction were heated at 350°–400° C. under air at 250 cc/min. for 15 minutes to give 2.2 g of yttrium oxide.

EXAMPLE II

Dry erbium benzoate, 10.6 g, 20 mmoles, treated under the same conditions as in Example I gave 3.7 g of solid product that analyzed 30.1 wt% benzophenone, 5.07 wt% anthraquinone, and 16.6 wt% o-dibenzoylbenzene. The tube contents remaining after extraction of product were oxidized at 350°–400° C. by air to recover 3.8 g of erbium oxide. Analysis was by gas chromatography.

EXAMPLE III

Dry dysprosium benzoate, 10.51 g, 20 mmoles, treated under the same conditions as in Example I, gave 4.0 g of product that analyzed 38.6 wt% benzophenone, 2.42 wt% anthraquinone, and 18.4 wt.% o-dibenzoylbenzene. The tube contents remaining after extraction of product were oxidized by air at 350°–400° C. to recover 3.72 g of dysprosium oxide.

EXAMPLE IV

The following example illustrates results obtained with use of benzoic acid salts other than the salts of the instant invented process.

Sodium benzoate, 7.2 g, 50 mmoles, was heated in a Vycor tube under nitrogen at 100 cc/min. No decomposition occurred up to 450° C. Heating at 475°–550° C. for 30 minutes and workup as in Example I gave 0.85 g of product that analyzed (g.c.) 1.7 wt% benzophenone, 33.9 wt% biphenyl, 1.85 wt% diphenylmethane, 2.0 wt% fluorene, and 0.47 wt% fluorenone, together with lesser amounts of terphenyl, quaterphenyl, and phenylated fluorenes. No anthraquinone or o-dibenzoylbenzene was detected. Most of the product was an insoluble char. Analysis was by gas chromatography.

EXAMPLE V

The procedure of Example IV was repeated using potassium benzoate. The results were similar to those obtained in Example IV.

Potassium benzoate, 8.0 g, 50 mmoles, was treated as in Example IV to give 0.65 g of soluble product that analyzed 0.13 wt% benzophenone, 51.4 wt% biphenyl, 0.9 wt% diphenylmethane, 7.1 wt% fluorene, 0.20 wt% fluorenone, and varying amounts of terphenyl, quaterphenyl, and phenylated fluorenes. No anthraquinone or o-dibenzoylbenzene was detected. Most of the product was insoluble char.

EXAMPLE VI

The following illustrates the process of the instant invention using substituted salts of benzoic acid. Yttrium salts of substituted benzoic acids were pyrolyzed in a Vycor tube under nitrogen at 100 cc/min. at 400°–600° C. for 2–10 minutes. The distillates were taken up in acetone, the cooled Vycor tube contents were extracted with acetone, the acetone extracts were filtered and evaporated. Residues were analyzed by mass spectrometry, with these results:

| Substituted Benzoic Acid (7g of Y salt in each case were pyrolyzed) | Wt. of Product g. | Products, % of Total | |
| --- | --- | --- | --- |
| o-toluic | 3.38 | 1.4% | dimethyl benzophenone |
|  |  | 57.5% | dimethyl anthraquinone |
| p-chloro | 2.03 | 26% | dichlorobenzophenone |
|  |  | 6.5% | dichloroanthraquinone |
|  |  | 14.7% | trichlorodibenzoylbenzene |
| p-fluoro | 2.25 | 20.4% | difluorobenzophenone |
|  |  | 3.6% | difluoroanthraquinone |
|  |  | 6.7% | trifluorodibenzoylbenzene |

EXAMPLE VII

The following illustrates a method of separation of the products of the instant invented process and subsequent purification.

20 g of yttrium benzoate was treated as in Example I, giving 7.7 g yellow solid as residue after acetone extraction of the pyrolysate. The yellow solid was distilled in vacuo; 2.96 g (38.4 wt%) of benzophenone distilled at 123°–127° C. at 2 Torr., solidifying in the condenser. It melted at 47°–49° C.

EXAMPLE VIII

The following illustrates the method of use of the oxides of yttrium, erbium, or dysprosium to obtain benzoate salts required as starting materials for the process of the instant invention.

A mixture of 2.2 g (9.74 mmoles) of yttrium oxide, obtained in Example I by air oxidation of the pyrolysis residue, and 3.66 g. (30 mmoles) benzoic acid was stirred in 200 ml of water at 85° C. for 26 hours. The mixture was cooled, the solid was collected on a filter, washed with two 20 ml portions of acetone, and dried, to give 4.21 g. (94 mole %) of yttrium benzoate.

EXAMPLE IX

This example illustrates an alternative process for continuous production of benzophenone, anthraquinone, and o-dibenzoylbenzene using benzoic acid and an oxide of yttrium, erbium, dysprosium or mixtures thereof in the presence of steam.

A mixture of steam, 2 parts, and benzoic acid, 1 part, is passed over 4.52 g. (20 mmoles) yttrium oxide in a Vycor tube at 500° C. until 12.2 g. (0.1 mole) benzoic acid has been added. Residence time is 8.7 seconds. The product is extracted with 5% aqueous sodium bicarbonate to remove unreacted benzoic acid, then filtered and dried. The aqueous solution is acidified with dilute sulfuric acid, filtered, washed with a little water and dried to recover 9.03 g., 0.074 mole, that could be recycled as benzoic acid. The product, which is insoluble in aqueous bicarbonate, 4.4 g., is analyzed by gas chromatography and consists of 40.1% benzophenone, 4.7% anthraquinone, and 17.1% o-dibenzoylbenzene.

What is claimed is:

1. A process for the synthesis of at least one compound of the group comprising benzophenone, anthraquinone, and o-dibenzoylbenzene compounds which comprises pyrolysis of a metal salt of a benzoic acid compound, said metal of said salt being selected from the group consisting essentially of yttrium, erbium, and dysprosium and mixtures thereof in an inert atmosphere at a temperature within the range of from about 200° C. to about 600° C. and a pressure of from about 0.1 to about 100 atmospheres.

2. The process of claim 1 wherein said metal salt of said benzoic acid compound is selected from the group consisting of yttrium benzoate, erbium benzoate, dysprosium benzoate, and mixtures thereof.

3. The process of claim 1 wherein said metal salt of said benzoic acid compounds comprises a substituted benzoic acid compound, substitutions of said compound being selected from the group consisting of halogens, methyl groups, and nitro groups.

4. The process of claim 3 wherein the said substituted compound is selected from the group consisting of yttrium o-toluate, yttrium p-chlorobenzoate, yttrium p-fluorobenzoate and mixtures thereof.

5. The process of claim 1 wherein products of said process are recovered by crystallization or distillation.

6. The process of claim 1 where said inert atmosphere comprises a gas selected from the group consisting of nitrogen, carbon dioxide, helium, argon, and mixtures thereof.

7. The process of claim 1 wherein said inert atmosphere comprises nitrogen.

8. A process for the synthesis of at least one compound of the group comprising benzophenone, anthraquinone, and o-dibenzoylbenzene compounds which comprises passing a benzoic acid compound in the presence of steam through a metal oxide selected from the group consisting of yttrium oxide, erbium oxide, dysprosium oxide, and mixtures thereof at a temperature within the range of from about 200° C. to about 500° C. and from about 0.1 to about 100 atmospheres.

9. The process of claim 8 wherein said benzoic acid compound comprises benzoic acid.

10. The process of claim 8 wherein said benzoic acid compound comprises a substituted benzoic acid compound, substitutions of said compound being selected from the group consisting of halogens, methyl groups, and nitro groups.

11. The process of claim 1 wherein said synthesis is a concurrent synthesis of at least two compounds of the group comprising benzophenone, anthraquinone, and o-dibenzoylbenzene compounds.

12. The process of claim 8 wherein said synthesis is a concurrent synthesis of at least two compounds of the group comprising benzophenone, anthraquinone, and o-dibenzoylbenzene compounds.

* * * * *